(12) United States Patent
Gao et al.

(10) Patent No.: US 7,879,088 B2
(45) Date of Patent: Feb. 1, 2011

(54) CAPSULAR BAG FOR ARTIFICIAL VITREOUS BODY AND METHOD FOR MANUFACTURING THE SAME

(75) Inventors: Qianying Gao, Guangzhou (CN); Shansang Mou, Guangzhou (CN)

(73) Assignee: Guangzhou Vesber Biotechnology Company, Co. Ltd., Baiyun District Guangzhou (CN)

( * ) Notice: Subject to any disclaimer, the term of this patent is extended or adjusted under 35 U.S.C. 154(b) by 637 days.

(21) Appl. No.: 11/657,774

(22) Filed: Jan. 24, 2007

(65) Prior Publication Data

US 2007/0173933 A1    Jul. 26, 2007

(30) Foreign Application Priority Data

Jan. 24, 2006    (CN) .................. 2006 1 0033296

(51) Int. Cl.
*A61F 2/14* (2006.01)
(52) U.S. Cl. ..................................... 623/4.1
(58) Field of Classification Search .............. 623/4.1, 623/5.11, 5.12, 5.16, 6.13, 6.64, FOR. 103
See application file for complete search history.

(56) References Cited

U.S. PATENT DOCUMENTS

| | | | | |
|---|---|---|---|---|
| 4,685,447 A | * | 8/1987 | Iversen et al. | 128/899 |
| 4,685,921 A | * | 8/1987 | Peyman | 623/6.13 |
| 4,902,292 A | * | 2/1990 | Joseph | 623/6.64 |
| 5,282,851 A | * | 2/1994 | Jacob-LaBarre | 623/6.56 |
| 2003/0036796 A1 | * | 2/2003 | Laguette et al. | 623/6.36 |
| 2005/0125059 A1 | * | 6/2005 | Pinchuk et al. | 623/6.56 |

FOREIGN PATENT DOCUMENTS

CN        1483388 A    *    3/2004

OTHER PUBLICATIONS

English translation of Gao et al., CN 1483388 A, published Mar. 24, 2004.*

* cited by examiner

*Primary Examiner*—David H. Willse
(74) *Attorney, Agent, or Firm*—Charles E. Baxley

(57) ABSTRACT

A capsular bag for the artificial vitreous body is made up of a material selected from the group consisting of polysiloxane, polyurethane styrene triblock copolymer thermoplastic elastomers, hydroxyethyl methacrylate, polyvinyl alcohol, poly (lactide-co-glycolide, and hyaluronic acid ester. A method for manufacturing the capsular bag for the artificial vitreous body is performed by dip-molding, effectively improving the smoothness of the inner surface of the capsule. An eye die is dipped into a gel solution until the surface adsorbs the gel, and then lifted, repeating 3-6 times. The dipped eye is hardened into shape. A shaped spherical outer capsule is peeled out of the eye die. The capsular bag for the artificial vitreous body has high biocompatibility and excellent flexibility.

11 Claims, 1 Drawing Sheet

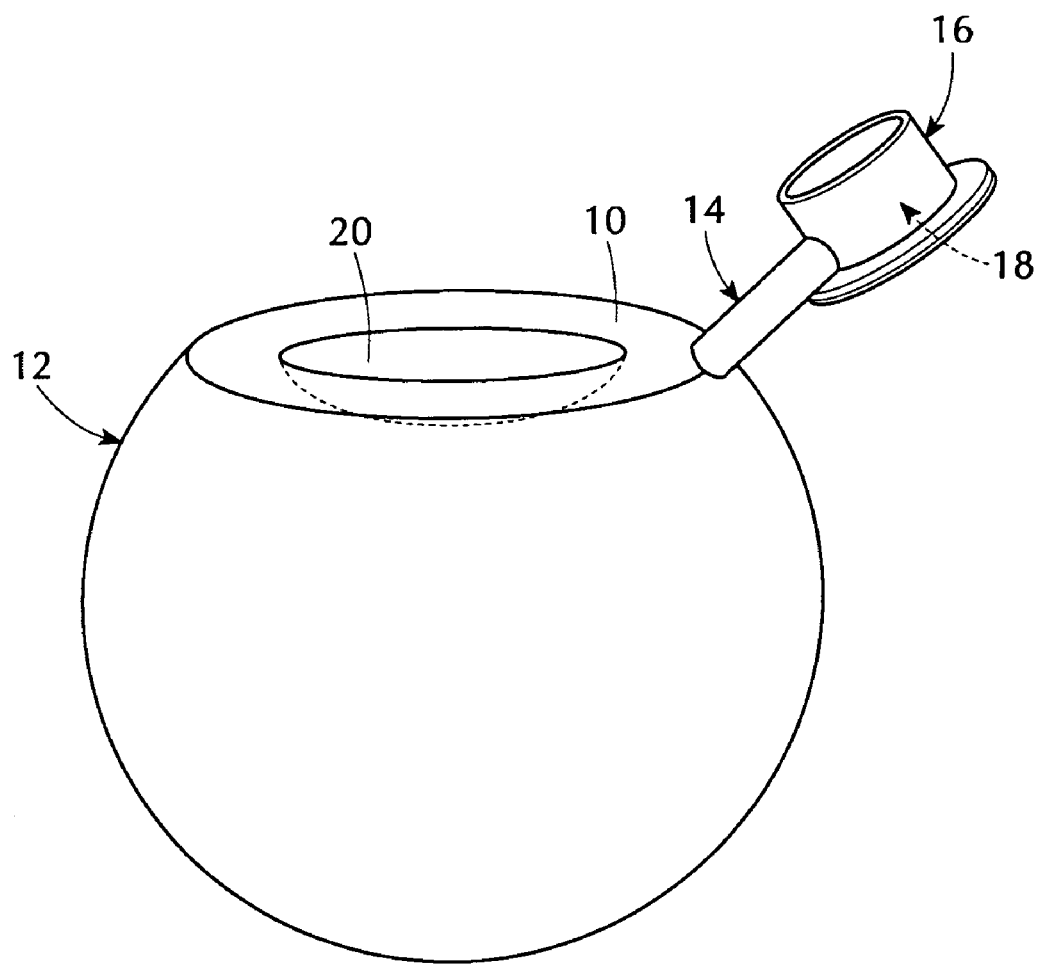

CAPSULAR BAG FOR ARTIFICIAL VITREOUS BODY AND METHOD FOR MANUFACTURING THE SAME

BACKGROUND OF THE INVENTION

1. Field of the Invention

The present invention relates to a medical biomaterial, particularly, to a capsular bag for artificial vitreous body, and a method for manufacturing the same.

2. Description of the Prior Art

Modern vitrectomy is a great revolution in ophthalmic therapy, thus allowing many ophthalmic disorders that would have previously been regarded as incurable to be cured. The operation indications thereof enlarge to several dozen kinds of ophthalmic disorders. It plays a great role in an ophthalmic clinic, and saves innumerable eyes that would go blind.

The normal vitreous body is a kind of gelatinous tissue that cannot regenerate. After vitrectomy, substitutes for vitreous body are required to fill the cavity of the removed vitreous body to support or plug the retina to prevent retinal detachment. Currently, national and international studies on substitutes for vitreous body are numerous, mainly including inert gas, silicone oil, heavy silicone oil, perfluorocarbon liquids, and hydrogels composed of high molecular weight hydrophilic polymers being the national or international research focus in the 1990s. Their therapy results, however, are not satisfying. Some of which could result in serious complications, for example, inert gas for instance C3F8 may easily cause a cataract, and lose the effect of tamponade at about two weeks after the surgery, such that it could not generate sustained top-pressure on the retina. Perfluorocarbon liquids are toxic to the retina, such that it would not settle in the cavity of vitreous body for a long time and could be utilized in surgery only. Additionally, perfluorocarbon liquids are easy to remain in the eyes and difficult to remove after reaction with water. Present substitutes for silicon oils widely used in clinics could result in glaucoma and cataract, and will self-emulsify within a particular time. The emulsified substitutes have to be removed. Upon removing, however, the retina can easily detach again. Repetitive surgeries not only aggravated the burden of patients, but also seriously impaired the vision of the patients. Even though the surgery is successful, the vision of the patients is very poor resulting from a low refractive index of silicon oil not generating adequate top pressure on the breaks underlying the retina, and that the diopter in the eyeball shifted to high hyperopia after tilling. Additionally, after surgeries, patients had to lie on their stomachs for a long time to prevent silicon oil from flowing into the anterior chamber, thus making the patients very agonized. Hydrogels mainly included PVP hydrogels, PVA hydrogels, PAM hydrogels, and Poly(1-vinyl-2-pyrrolidone) hydrogels, and so on. These hydrogels, however, are still at the experimental stage in opthalmology, and so far no one of these hydrogels has performed in clinic application, resulting in lack of observation on the long-term therapeutic effect on the toxicity to the eyes, and the price is very high. The patients could not afford it. Finding vitreous substitutes that met physiological needs and are more economical are required, which is one of the problems disturbing the doctors for vitreous retinal disorders in this century.

How to make an artificial vitreous body of which both structure and function are the same as those of the natural vitreous body is one of the keys to ensure the success of vitrectomy. Up to now, the components of the vitreous body have not been fully known. Based on the conditions of modern science and technology, the need to make an artificial vitreous body of which both structure and function are perfect is impractical. Therefore, without pursuing to make a fully physiological artificial vitreous body, the research thinking is changed to restore the most important function of the vitreous body, i.e., support of the retina so as to avoid repetitive retinal detachment, which is also a method to resolve the problem.

The current substitutes for a vitreous body are sometimes called an artificial vitreous body. Implantation methods are performed by directly injecting the substitutes for the vitreous body into the cavity of the vitreous body to support the retina to prevent the retina from detaching again. Chinese patent No. ZL 03126845.5 discloses a technical scheme about a capsular artificial vitreous body, which utilizes a system of an artificial vitreous body comprising a capsular bag made of high molecular weight film filled with water and having a drainage valve to achieve the object of supporting the retina and preventing the retina from detaching again. The capsular bag accommodates the shape and volume of the cavity of the human eyes. A drainage tube provided with a drainage valve is connected to the top of the capsular bag. The capsular bag and the drainage tube are hidden inside an assistant implanting means, i.e., an ejector handle. The head of the ejector handle can clamp the capsular bag. Since the capsular bag is manufactured manually with acetic acid and vinyl acetate copolymer, however, the technical scheme still has drawbacks, such as low biocompatibility and poor flexibility.

SUMMARY OF THE INVENTION

The object of the present invention is to overcome the drawbacks of the prior art, and to provide a capsular bag for an artificial vitreous body with high biocompatibility and excellent flexibility, and a method for manufacturing the same.

The object of the present invention is carried out as follows:

The capsular bag for the artificial vitreous body is mainly made up of a material selected from the group consisting of polysiloxane, polyurethane, styrene triblock copolymer thermoplastic elastomers, hydroxyethyl methacrylate (HEMA), polyvinyl alcohol (PVA), poly (lactide-co-glycolide) (PLGA), and hyaluronic acid ester.

The capsular bag for the artificial vitreous body has an anteroposterior diameter of 14-18 mm, a horizontal diameter of 20-25 mm, and a vertical diameter of 20-25 mm. The front face is concave with a curvature radius of 4-8 mm.

The wall of the capsular bag for the artificial vitreous body is 10-50 um thick. The shore hardness of the capsular bag is 5-40 degrees. The tensile strength is 4-12 Mpa. The hemolysis rate of material is not more than 5%. The transmission rate is not less than 90%. The fog density is not more than 0.1%. The elongation is not less than 1000%. The tear strength is 10-40 kN/m.

The top of the capsular bag for the artificial vitreous body is connected to a drainage tube. The drainage tube is provided with a drainage valve made up of a material selected from the group consisting of polysiloxane, polyurethane, styrene triblock copolymer thermoplastic elastomers, hydroxyethyl methacrylate (HEMA), polyvinyl alcohol (PVA), poly (lactide-co-glycolide) (PLGA), and hyaluronic acid ester. The drainage tube has 2-5 mm of length and a 0.1-0.3 mm inner diameter, as well as a 0.4-0.7 mm outer diameter. The diameter of the body of the drainage valve is 2-4 mm, with 1-3 mm of height.

The styrene triblock copolymer thermoplastic elastomers is a material selected from the group consisting of styrene-ethylene/butadiene-styrene triblock copolymer (SEBS), styrene-isoprene butadiene-styrene triblock copolymer (SIS), styrene-ethylenel/propylene-styrene triblock copolymer (SEPS), and styrene-butadiene-styrene triblock copolymer (SBS).

Preferably, the capsular bag for the artificial vitreous body and the drainage tube are made up of polysiloxane.

As an improvement to the present invention, materials of the capsular bag for the artificial vitreous body, such as polysiloxane or polyurethane, are modified by adding hydroxy (—OH)-containing hydrophilic groups, to control water rate in the capsular bag such that the water rate is 5-30%. Fluoro group-containing materials are added into the materials of polysiloxane or polyurethane to increase oxygen permeability of the capsular bag. A drug sustained release system (DDS) is formed by changing the thickness and crosslink density of the materials of the capsular bag for the artificial vitreous body, increasing osmotic pressure inside the capsular bag to control the sustained release result of the capsular bag, and by injecting therapeutic drugs via the drainage valve.

The method for manufacturing the capsular bag for the artificial vitreous body is performed with dip-molding, comprising the following steps:

(1) an eye die is dipped into a gel solution until the surface thereof absorbs the gel, and is then lifted, repeating the step 3-0 times;

(2) the dipped die is hardened to shape;

(3) the shaped spherical outer capsule is peeled out of the eye die.

The capsular bag for the artificial vitreous body of the present invention has the following advantages:

(1) Safety with low toxicity. Since restricted by the capsular bag, the substitutes for the vitreous body are not in contact with the ophthalmic tissues, thus avoiding the effect of current substitutes for the vitreous body on the anterior segment. The capsular bag is easy to remove completely. If the patient cannot endure the serious reaction in the eyes, the capsular bag could be removed easily, thus avoiding the current substitutes for the vitreous body remaining in the eyes due to difficulty removing.

(2) Good result of top pressure on the retina. Because expanding evenly, the capsular bag could generate sustained top pressure on retinal breaks in any position so as to decrease the recrudescent chances of retinal detachment and increase the cure rate of the operation, which largely alleviates the patients' financial burden by avoiding repetitive operations;

(3) The drainage valve of the artificial vitreous body controls the pressure inside the capsular bag. If the pressure is more than 20 mmHg, the liquid in the capsular bag flows out automatically such that the pressure inside the capsular bag is adjusted at 12-20 mmHg.

(4) The artificial vitreous body is skillfully integrated with the drug sustained release system.

(5) The capsular bag for the artificial vitreous body and the drainage valve are manufactured by application of absorbable materials, such as poly (lactide-co-glycolide) (PICA), and hyaluronic acid, which could be degraded within 60-90 days and absorbed completely.

In conclusion, according to the present invention, the capsular bag for the artificial vitreous body that is made of modified polysiloxane elastomers has high biocompatity and excellent flexibility. After implantation of the artificial vitreous body system, animal experiments proved that it could be implanted and removed easily without significant histological toxicology reaction by examining by electrophysiology, light microscopy, and electron microscopy. The intraocular pressure can be adjusted via the drainage valve that is fixed to underlay the conjunctive after the operation. The fabricating procedure is carried out by the method for dipped-molding, effectively improving the smoothness of the inner surface of the capsular bag. This manufacture is easy to operate and its repeatability is attractive.

BRIEF DESCRIPTION OF THE DRAWINGS

The sole FIGURE of the drawing is a diagrammatic perspective view of the capsular bag for the artificial vitreous body of the present invention.

DESCRIPTION OF THE PREFERRED EMBODIMENT

As shown in the sole FIGURE, which is a diagrammatic perspective view of the capsular bag for the artificial vitreous body of the present invention, the front surface 10 of the capsular bag 12 for the artificial vitreous body is connected to a drainage tube 14. The drainage tube 14 is provided with a drainage valve 16. The bottom of the body is embedded with a steel barrier 18 to prevent the body from being perforated by the injector pins to ensure the gas-tightness of the body.

Example 1

According to the present example, the capsular bag 12 for the artificial vitreous body and the drainage tube 14 on it and the drainage valve 16 are made up of polysiloxane. The arteroposterior diameter of the artificial vitreous body is 16 mm and the horizontal diameter thereof is 22 mm and the vertical diameter thereof is 23 mm. The front surface 10 thereof is concave at 20 with a curvature radius of 6 mm. The thickness of the wall of the capsular bag 12 for the artificial vitreous body is 50 um. Shore hardness of the material for the artificial capsular bag 12 is 30 degrees. The tensile strength is 5 Mpa. The elongation is more than 1000%. The tear strength is about 35 kN/m. The hemolysis rate of the material is about 4%. The transmission rate is 95%. The fog density is less than 0.1%. The drainage tube 14 on the capsular bag 12 for the artificial vitreous body is 3 mm long and the inner diameter thereof is 0.2 mm and the outer diameter thereof is 0.57 mm. The body of the drainage valve 16 has a diameter of 3 mm and a height of 2 mm.

Polysiloxane is a transparent high molecular weight polymer with high biocompatibility, excellent forming technology and flexibility, and without generation and escape of low molecular weight during formation of the sulfide crosslink. The biological evaluation experiments showed a negative reaction. The material has no significant toxicity. No potentially sensitive substances are contained in the material. Pyrogen content therein is in accordance with the requirement of an organism. Polysiloxane is a satisfactory candidate material for the artificial vitreous body. The manufactured artificial vitreous body can be infused with physiological saline solution via the drainage valve 16 to fill the capsular bag 12 and simultaneously adjust the pressure inside the capsular bag 12.

The present capsular bag 12 for the artificial vitreous body is manufactured by the following steps:

A die specific for human eyes is used. The surfaces and corners of the die should be as smooth as possible to facilitate the smoothness of the inner surface of the capsule. The die is slowly dipped into the polysiloxane gel solution and lifted until the surface thereof absorbs the gel. The dipping and lifting procedures are repeated 5 times with moderate force and speed to prevent generation of bubbles. Then, it is placed into an oven and heated to harden into shape. The hardening conditions are a temperature of 100 degrees for two hours.

Finally, the shaped outer capsule is peeled out of the die, thus obtaining the capsular bag 12 for the artificial vitreous body.

The drainage valve 16 is manufactured according to the prior art press molding.

Example 2

According to the present example, the capsular bag 12 for the artificial vitreous body and the drainage tube 14 on it and the drainage valve 16 are made up of poly(lactide-co-glycolide). The anteroposterior diameter of the artificial vitreous body is 18 mm, the horizontal diameter thereof is 25 mm, and the vertical diameter thereof is 25 mm. The front face thereof is concave at 20 with 7 mm of curvature radius. The thickness of the wall of the capsular bag 12 for the artificial vitreous body is 50 um. Shore hardness of the material for the artificial capsular bag 12 is 40 degrees. The tensile strength is 5 Mpa. The elongation is more than 1000%. The tear strength is about 35 kN/m. The hemolysis rate of the material is about 2%. The transmission rate is 93%. The fog density is less than 0.1%. The drainage tube 14 on the capsular bag 12 for the artificial vitreous body is 5 mm long, the inner diameter is 0.25 mm, and the outer diameter is 0.65 mm. The diameter of the body of the drainage valve 16 is 3.5 mm and the height is 2.5 mm.

The present capsular bag 12 for the artificial vitreous body is manufactured by the following steps:

A die specific for human eyes is used. The surfaces and corners of the die should be as smooth as possible to achieve smoothness of the inner surface of the capsule. The die is slowly dipped into the poly (lactide-co-glycolide) gel solution and lifted until the surface thereof absorbs the gel. The dipping and lifting procedures are repeated 5 times with moderate force and speed to prevent generation of bubbles. Then it is placed into an oven and heated to harden to shape. The hardening conditions are a temperature of 85 degrees for three hours. Finally, the shaped outer capsule is peeled out of the die, thus obtaining the capsular bag 12 for the artificial vitreous body.

The drainage valve 16 is manufactured according to the method described in example 1.

Example 3

According to the present example, the capsular bag 12 for the artificial vitreous body and the drainage tube 14 on it and the drainage valve 16 are made of styrene-ethylene/butadiene-styrene triblock copolymer (SEBS). The anteroposterior diameter of the artificial vitreous body is 14.5 mm and the horizontal diameter thereof and the vertical diameter thereof are 21 mm. The front surface 10 thereof is concave at 20 with 4.5 mm of curvature radius. The thickness of the wall of the capsular bag 12 for the artificial vitreous body is 50 um. Shore hardness of the material for the artificial capsular bag 12 is 15 degree degrees. The tensile strength is 5 Mpa. The elongation is more than 1000%. The tear strength is about 35 kN/m. The hemolysis rate of the material is about 2%. The transmission rate is 95%. The fog density is less than 0.1%. The drainage tube 14 on the capsular bag 12 for the artificial vitreous body is 3 mm long and the inner diameter thereof is 0.15 mm and the outer diameter thereof is 0.45 mm. The diameter of the body of the drainage valve 16 is 2 mm and the height thereof is 1.5 mm.

The present capsular bag 12 for the artificial vitreous body is manufactured by the following steps:

A special die for human eyes is used. The surfaces and corners of the die should be as smooth as possible to achieve smoothness of the inner surface of the capsule. The die is slowly dipped into the polysiloxane gel solution and lifted until the surface thereof absorbs the gel. The dipping and lifting procedures are repeated 5 times with moderate force action and speed to prevent generation of bubbles. Then it is placed into an oven and heated to harden to shape. The hardening conditions are a temperature of 110 degrees for three hours. Finally, the shaped outer capsule is peeled out of the die, thus obtaining the capsular bag 12 for the artificial vitreous body.

Example 4

According to the present example, the capsular bag 12 for the artificial vitreous body and the drainage tube 14 on it and the drainage valve 16 are made of modified polyurethane containing hydroxy (—OH) hydrophilic groups. The anteroposterior diameter of the artificial vitreous body is 15 mm, the horizontal diameter thereof is 22 mm, and the vertical diameter thereof is 23 mm. The front face thereof is concave at 20 with a curvature radius of 5 mm. The thickness of the wall of the capsular bag 12 for the artificial vitreous body is 40 um. Shore hardness of the material for the artificial capsular bag 12 is 25 degrees. The tensile strength is 6 Mpa. The elongation is more than 1000%. The tear strength is about 35 kN/m. The hemolysis rate of the material is about 3%. The transmission rate is 95%. The fog density is less than 0.1%. The drainage tube 14 on the capsular bag 12 for the artificial vitreous body is 3.5 mm long, the inner diameter thereof is 0.2 mm, and the outer diameter thereof is 0.5 mm. The diameter of the body of the drainage valve 16 is 2.5 mm and the height is 2 mm. The water content in the capsular bag 12 is 10%.

The present capsular bag 12 for the artificial vitreous body is manufactured by the following steps:

A special die for human eyes is used. The surfaces and corners of the die should be as smooth as possible to achieve smoothness of the inner surface of the capsule. The die is slowly dipped into the gel solution composed of modified polyurethane containing hydroxy (—OH) hydrophilic groups and lifted until the surface thereof absorbs the gel. The dipping and lifting procedures are repeated 5 times with moderate force and speed to prevent generation of bubbles. Then, it is placed into oven and heated to harden to shape. The hardening conditions are a temperature of 105 degrees for 3.5 hours. Finally, the shaped outer capsule is peeled cut of the die, thus obtaining the capsular bag 12 for the artificial vitreous body.

According to the present invention, the capsular bag 12 for the artificial vitreous body can be filled with physiological saline solution via the drainage valve 16 and adjust the top pressure on the retina inside the capsular bag 12 to an appropriate level.

After implantation of the artificial vitreous body system prepared by the capsular bag 12 according to the prevent invention, animal experiment proved that it could be implanted and removed easily without a significant histological toxicology reaction by being examined by electrophysiology, light microscopy, and electron microscopy.

The capsular bag 12 for the artificial vitreous body manufactured by the examples 1-4 can control the sustained release result of the capsular bag 12 by methods for changing the thickness and crosslink density of the materials of the capsular bag 12 for the artificial vitreous body and increasing osmotic pressure inside the capsular bag 12, and can be infused with drugs via the drainage valve 16 such that the capsular bag 12 for the artificial vitreous body becomes a drug sustained release system (DDS).

Since restricted by the capsular bag 12, the substitutes for the vitreous body are not in contact with the ophthalmic tissues, thus avoiding the effect of current substitutes for the vitreous body on the anterior segment. If a patient cannot endure the serious reaction in the eyes, the vitreous body can be removed easily, thus avoiding the current substitutes for the vitreous body remaining in the eyes due to difficulty removing.

Because it can expand evenly, the capsular bag 12 can generate sustained top pressure on retinal breaks in any position so as to decrease the recrudescent chances of retinal detachment and increase the cure rate of the operation, which would largely alleviate the patients' financial burden due to avoiding repetitive operations.

What is claimed is:

1. An artificial vitreous body, comprising:
   a) a capsular bag; and
   b) as drainage tube;
   wherein said capsular bag is made up of a material selected from the group consisting of polysiloxane, polyurethane, styrene triblock copolymer thermoplastic elastomers, hydroxyethyl methacrylate, polyvinyl alcohol, poly (lactide-co-glycolide), and hyaluronic acid;
   wherein a front surface of said capsular bag is connected to said drainage tube;
   wherein said drainage tube is provided with a drainage valve that has a body; and
   wherein a bottom of said body of said drainage valve of said drainage tube is embedded with a steel barrier to prevent said body of said drainage valve of said drainage tube from being perforated by an injector pin so as to ensure gas-tightness of said body of said drainage valve of said drainage tube.

2. The artificial vitreous body according to claim 1, wherein said capsular bag has an anteroposterior diameter of 14-18 mm, a horizontal diameter of 20-25 mm, a vertical diameter of 20-25 mm, and said front surface is concave with a 4 to 8 mm radius of curvature.

3. The artificial vitreous body according to claim 1, wherein a wall of said capsular bag is 10-50 um thick; tensile strength is 4-12 Mpa; fog density is not more than 0.1%; elongation is not less than 1000%; and tear strength is 10-40 kN/m.

4. The artificial vitreous body according to claim 1, wherein said drainage valve of said drainage tube is made up of a material selected from the group consisting of polysiloxane, polyurethane, styrene triblock copolymer thermoplastic elastomers, hydroxyethyl methacrylate, polyvinyl alcohol, poly (lactide-co-glycolide), and hyaluronic acid.

5. The artificial vitreous body according to claim 1, wherein said drainage tube has a length of 2-5 mm, an inner diameter of 0.1-0.3 min and an outer diameter of 0.4-0.7 mm; said body of said drainage valve of said drainage tube has a diameter of 2-4 mm and a height of 1-3 mm.

6. The artificial vitreous body according to claim 1, wherein the styrene triblock copolymer thermoplastic elastomers are a material selected from the group consisting of styrene-ethylene/butadiene-styrene triblock copolymer, styrene-isoprene butadiene-styrene triblock copolymer, styrene-ethylene/propylene-styrene triblock copolymer, and styrene-butadiene-styrene triblock copolymer.

7. The artificial vitreous body according to claim 1, wherein said capsular bag and said drainage tube are made up of polysiloxane.

8. The artificial vitreous body according to claim 1, wherein fluoro-group containing materials are added into one of the polysiloxane and the polyurethane to increase oxygen permeability of the capsular bag.

9. The artificial vitreous body according to claim 1, wherein hydroxy (—OH)-containing hydrophillic groups are added into materials of said capsular bag, including one of the polysiloxane and the polyurethane, to control a water rate in said capsular bag so as to allow the water rate to be 5-30%.

10. The artificial vitreous body according to claim 1, wherein said capsular bag and said drainage valve of said drainage tube are manufactured by application of absorbable materials selected from the group consisting of poly (lactide-co-glycolide) and hyaluronic acid, and is degraded within 60-90 days and absorbed completely.

11. The artificial vitreous body according to claim 1, wherein said capsular bag is infused with therapeutic drugs via said drainage valve of said drainage tube so as to allow said capsular bag to be a drug sustained release system.

* * * * *